US006454756B1

(12) United States Patent

Sasaki

(10) Patent No.: US 6,454,756 B1

(45) Date of Patent: Sep. 24, 2002

(54) INJECTOR OF SPERM FOR ARTIFICIAL INSEMINATION OR FERTILIZED OVUM FOR TRANSPLANTATION OF DOMESTIC ANIMAL AND METHOD OF OPERATING THEREOF

(75) Inventor: Katsuhiko Sasaki, Fujimi-mura (JP)

(73) Assignee: Livestock Improvement Association of Japan, Inc., Tokyo (JP)

(*) Notice: Subject to any disclaimer, the term of this patent is extended or adjusted under 35 U.S.C. 154(b) by 0 days.

(21) Appl. No.: 09/578,193

(22) Filed: May 24, 2000

(30) Foreign Application Priority Data

Jul. 9, 1999 (JP) .......................................... 11-195969

(51) Int. Cl.[7] ............................................. A61M 31/00

(52) U.S. Cl. ...................................... 604/514; 604/515

(58) Field of Search ................................ 604/514, 515, 604/516, 517, 612, 187, 188, 193, 194, 195, 196, 197, 198, 199, 233–240

(56) References Cited

U.S. PATENT DOCUMENTS 3,877,464 A * 4/1975 Vermes .......................... 128/2
4,416,660 A * 11/1983 Dafoe ........................ 604/515
4,574,000 A * 3/1986 Hunter ........................ 623/12
4,637,818 A * 1/1987 Johnson et al. ............. 417/550
4,832,681 A * 5/1989 Lenck .......................... 600/34
5,005,583 A * 4/1991 Bustillo ...................... 600/551
5,108,366 A * 4/1992 Schatz ......................... 604/28
5,147,315 A * 9/1992 Weber ......................... 600/35
5,904,665 A * 5/1999 Muharib ..................... 604/104
6,033,413 A * 3/2000 Mikus et al. .......... 604/102.01
6,146,378 A * 11/2000 Mikus et al. ............... 600/585

FOREIGN PATENT DOCUMENTS

JP 61-36935 8/1986
JP 62-107819 7/1987

* cited by examiner

*Primary Examiner*—Teresa Walberg
*Assistant Examiner*—Daniel Robinson
(74) *Attorney, Agent, or Firm*—Arter & Hadden LLP

(57) ABSTRACT

The injector of the present invention (10) comprises a heat-retaining tube (12), an outer pipe (18) for inserting into a uterus which is fixed parallel to a front end of the heat-retaining tube (12), a syringe (22) for injection inserted into the heat-retaining tube (12) from the rear end of the heat-retaining tube (12), an elastic and flexible tube for injection (24) which is connected to the front end of the syringe (22) and is pulled out of the front end of the heat-retaining tube and is inserted slidably into inside of the hollow of the outer pipe (18),and a discharge nozzle (28) which is mounted integrally to the front end of the tube (24) and projects from the front end of the tube (18), and in which a portion between a projecting position from the heat-retaining tube (12) and the outer pipe (18) is regarded as a surplus length portion (24*a*) and the surplus length portion (24*a*) is paid out in a state that the outer pipe (18) is inserted to a given depth in a uterus, thereby making the discharge nozzle (28) reach to the deep portion of the uterus along the shape of the uterus.

9 Claims, 8 Drawing Sheets

(Portion A, Magnified cross-section)

(Portion B, Magnified cross-section)

INJECTOR OF SPERM FOR ARTIFICIAL INSEMINATION OR FERTILIZED OVUM FOR TRANSPLANTATION OF DOMESTIC ANIMAL AND METHOD OF OPERATING THEREOF

BACKGROUND OF THE INVENTION

1. Field of the Invention

The present invention relates to an injector of a sperm for artificial insemination or a fertilized ovum for transplantation of a domestic animal such as cattle and the like and a method of operation therefor.

2. Description of the Related Art

Semen of so-called bull used for an artificial insemination is extremely valuable and expensive and is conserved in freezing state in an elongate sealed tube called a straw and is thawed at the time of artificial insemination when using. As an operation of injection of this semen into a uterus of a cow, a rectovaginal method has been generally used.

An operation of injection of semen of an ox by the rectovaginal method is described below referring to FIG. 10. FIG. 10 shows a cross section of a part of a uterus of a cow and reference numeral 1 denotes a rectum of a cow; 2 denotes a narrow and hourglass figure cervical canal positioned at an inlet of a uterus; 3 denotes a corpus uteri positioned at the back of the cervical canal; 4 denotes a pair of cornu uteri which is bifurcated from inner part of corpus uteri 3 and which are curved hemispherically.

A conventional injector of semen comprises an elongated narrow pipe 5 of small diameter, an injection tube 6 screwed to the front end of the pipe 5 and having a semen discharge opening perforated at the front end thereof, and a push bar 7 which is slidably inserted into a rear end of the pipe 5. A straw is provided inside the injection tube 6 in such a manner that a front end of the push bar 7 is to be inserted into the rear end of the straw to push and carry a cotton plug in the straw.

In injection operation, one hand is first inserted into a rectum 1 through an anus to grasp the cervical canal 2, then the rear end of the pipe 5 of small diameter is grasped and pushed by the other hand to insert the front end of the pipe 5 into a uterus. Then, the front end of the pipe 5 is penetrated through the cervical canal 2 while ascertaining the position of the front end of the pipe 5 by feeling of the one hand at a position of the cervical canal 2, and the front end of the pipe 5 is stopped short of reaching a cornu uteri 4. Thereafter, by pushing forward the push bar 7 exposed outside from the rear end of the pipe 5, a cotton plug in the rear end of the straw is pushed forward, thereby discharging semen in the straw from the semen discharge opening of the injection tube 6 into the uterus.

As a transplanter of a fertilized ovum for a cow, what is described in Japanese Examined Patent Publication No.61-36935 is publicly known. This transplanter is constructed by placing an inner pipe slidably in an outer pipe, the inner pipe having a front end which is rounded and sealed and being perforated with a small hole in a side of the end. This transplanter is also constructed so that a flexible tube inserted inside of the inner pipe may project through the aforementioned small hole.

When using, a fertilized ovum which is conserved by freezing in a straw is thawed, which is then sucked from the straw into a rear end of the flexible tube by using an attachment, and a syringe is fitted to the rear end of the tube. At the time when the outer pipe of this transplanter is inserted in a uterus of a cow, the small hole formed in the side of the front end of the inner pipe is covered with the outer pipe. Under this situation, the outer pipe is inserted into an inlet of cornu uteri in corpus uteri, and then the outer pipe is moved backward relative to the inner pipe to expose the small hole formed in the side of the front end of the inner pipe. Thereafter, the flexible tube is paid out forward from the back to project the front end of the tube outward through the small hole of the inner pipe so that the front end of this tube can reach to the depths of the uterus. Under this situation, air is supplied in the tube by operating a syringe, thereby injecting the fertilized ovum into the depths of cornu uteri from the front end of the tube.

However, since the pipe of small diameter in the aforementioned semen injector can only be inserted to stop short of reaching a cornu uteri, insemination rate has been relatively low.

It is possible to inject a fertilized ovum into the depths of uterus in the latter transplanter of fertilized ovum. However, since it is in double pipe construction comprising an outer pipe and an inner pipe, the outer pipe becomes thick having relatively large outer diameter. Therefore, when the outer pipe is inserted through a cervical uteri, there have been problems that insertion is relatively difficult and simultaneously endometrium might be injured.

Further, since there is a limit to enlarge the inner diameter of the inner pipe, the tube to be inserted therein is too narrow and weak to lead into the depths of cornu uteri certainly.

Furthermore, since it is not possible in the latter transplanter to confirm from the outside whether or not the opening of the small hole formed in the side of the front end of the inner pipe faces properly downward, there is a case where the small hole does not face downward because its position is shifted after insertion. In this case, the tube projected through the small hole is not inserted properly into the depths of cornu uteri. When the small hole faces upward, there is a case where the tube comes to contact with upper wall of corpus uteri and it returns to the inlet side. Therefore, the operation of the transplanter of the prior art has been very difficult.

Further, when this kind of operation is carried out outdoors in the cold latitudes, especially in case of the latter transplanter, since a fertilized ovum sucked into the tube from the thawed straw is exposed directly to the air in long-distance through the tube, there has been a risk that the fertilized ovum is shocked by temperature to be inactivated.

The present invention has been achieved taking the aforementioned problems into consideration.

SUMMARY OF THE INVENTION

Therefore, a first object of the present invention is to provide an injector of a sperm for artificial insemination or a fertilized ovum for transplantation of a domestic animal such as cattle and the like which can inject surely semen or a fertilized ovum into the depths of cornu uteri without injuring endometrium.

A second object of the present invention is to provide an injector of a sperm for artificial insemination or a fertilized ovum for transplantation of a domestic animal which is excellent in operability and can relieve temperature shock even when the operation of insertion of semen or a fertilized ovum into a uterus is carried out outdoors in the cold latitudes and a method of operating therefor.

In order to achieve the above-described objects, an injector of a sperm for artificial insemination or a fertilized ovum for transplantation of a domestic animal of the present invention comprises an outer pipe, a flexible tube inserted and placed inside of the outer pipe to be freely pushed out, a nozzle body mounted integrally to a front end of the flexible tube, the nozzle body having a closed front end which is formed in a shape of spherical surface and having a rear end connected to the flexible tube, the nozzle body further having in a side of the nozzle a perforated hole connected to the flexible tube, and a pushing means adapted to be connected with a rear end of the flexible tube for sending forward the sperm or ovum, the flexible tube being pushed forward from the rear end of the outer pipe after insertion of the outer pipe into a corpus uteri of the domestic animal, thereby paying out the flexible tube forward from the front end of the outer pipe to send nozzle body to a deep portion of a cornu uteri and thereafter to discharge the sperm or ovum from the perforated hole of the nozzle body into the deep portion of the cornu uteri through inside of the flexible tube by the pushing means.

Preferably, the flexible tube extends outside beyond the rear end of the outer pipe, the extended part of the flexible tube allowing to be pinched by finger tips and pushed forward by the finger tips.

Preferably, a heat-retaining tube is fitted to an outer peripheral surface of the rear end of the outer pipe, and the rear end of the flexible tube extends rearward from the rear end of the outer pipe and goes into the heat-retaining tube from the front end of the heat-retaining tube by making approximately one turn between the outer pipe and the heat-retaining tube.

Preferably, the one turn of the flexible tube defines a length of the flexible tube to be paid out from the front end of the outer pipe, the length of the flexible tube corresponding to the distance from the inside of the cervical canal to the deep portion of the cornu uteri.

Preferably, the injector further comprises a straw containing a sperm or ovum and removably attached between the rear end of the flexible tube and the pushing means to be contained in the heat-retaining tube.

More preferably, the heat-retaining tube is made from a transparent material.

Preferably, socket members adaptable to straws of different calibers is mounted removably to the front end and rear end of the straw respectively, and the straw is joined to the flexible tube and the pushing means respectively through each socket member.

Preferably, an effective substance for maintaining activity of a sperm or an ovum is previously injected into the pushing means before the straw is joined thereto.

Also, according to the present invention, a method of operating an injector set forth above is provided, wherein an outer periphery of the outer pipe is covered with a first plastic bag which is watertight, transparent and thin and the front end of which is sealed, an outer periphery of the heat-retaining tube is covered with a second plastic bag which is watertight, transparent and thin and the rear end of which is sealed, and the outer pipe of the injector is inserted in a given length into a uterus of a domestic animal in a state that an overlapped portion of both transparent plastic bags is sealed through a banding means, then the first plastic bag is moved relatively to the outer pipe to break a sealed portion of the front end of the first plastic bag, thereafter the flexible tube is picked with fingertips from outside of said second plastic bag, thereby pushing to send forward the flexible tube.

BRIEF DESCRIPTION OF THE DRAWINGS

For a more complete understanding of the present invention, reference may be made to the following detailed explanations in connection with the accompanying drawing in which.

PREFERRED EMBODIMENTS OF THE INVENTION

Referring now to the accompanying drawings, preferred embodiments of the present invention are described in detail.

Figure 1:
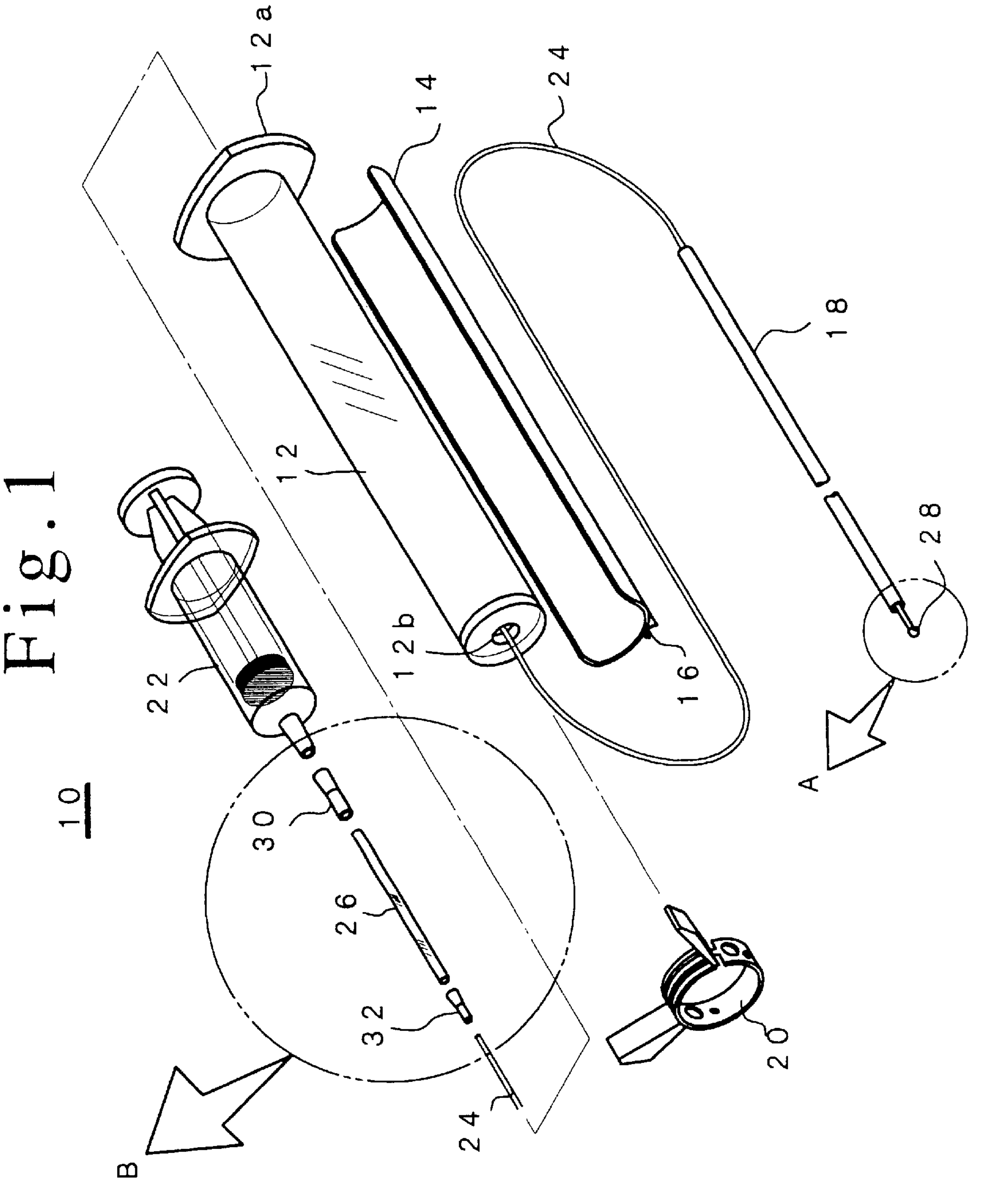
FIG. 1 is an exploded perspective view showing a whole structure of a semen injector of the present invention.
Figure 2:
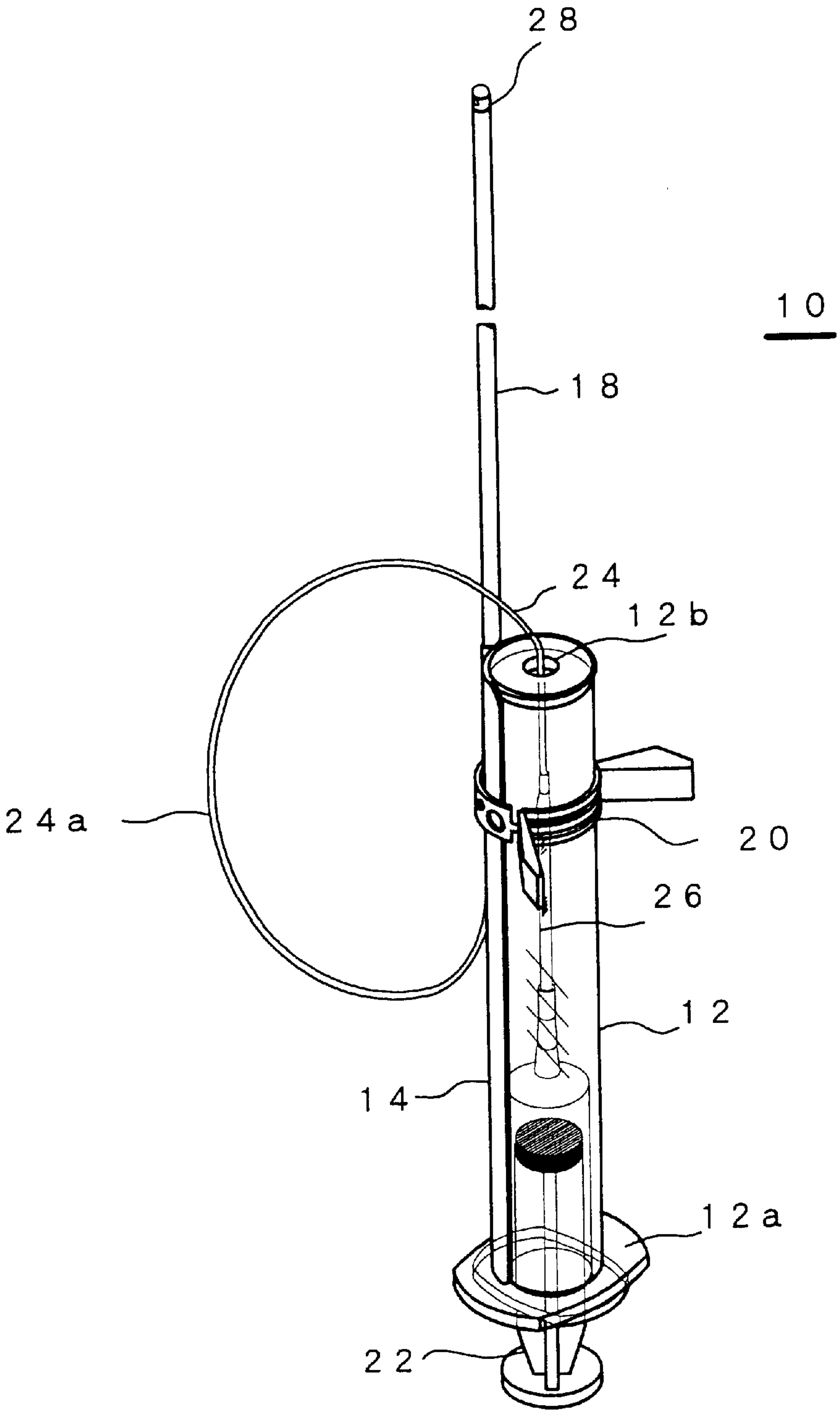
FIG. 2 is a perspective view showing an assembled semen injector of the present invention.

FIG. 1 and FIG. 2 show a whole structure of an injector of sperm of an ox for an artificial insemination of the present invention, in which FIG. 1 is an exploded perspective view and FIG. 2 is a perspective view showing an assembled semen injector of the present invention.

In FIGS. 1 and 2, an injector 10 comprises a heat-retaining tube 12, a protecting cover 14 covering approximate half outer periphery of the heat-retaining tube 12, a holder member 16 mounted to the lower front part of the protecting cover 14, an outer pipe 18 a rear part of which is fitted to the holder member 16, a pinch cock 20 which is fitted removably to outer peripheries of the heat-retaining tube 12 and the protecting cover 14 for fixing the outer pipe 18 to the holder member 16, a flexible tube 24 for semen injection a front part of which is inserted into the outer pipe, a syringe 22 a hollow barrel of which is inserted into the rear end of the heat-retaining tube 12, and a semen straw 26 one end of which is connected to a front end of the syringe 22 and the other end of which is connected to the flexible tube 24 for semen injection.

The heat-retaining tube 12 is provided with a flange 12*a* at its rear end opening and in the front end of which a small hole 12*b* is perforated. The heat-retaining tube 12 serves for two purposes of heat insulation and protection of the syringe 22 and the straw 26 which are contained therein. The heat-retaining tube 12 is made from a transparent acrylic resin so that visual observation of the inside can be performed with the syringe 22 and the straw 26 inserted therein.

The protecting cover 14 serves for two purposes of heat insulation and position maintenance of the outer pipe 18 and is formed in a half-round tube of a stainless steel sheet so as to fit to the outer periphery of the heat-retaining tube 12. The holder member 16 is fixed integrally to the lower front part of the protecting cover 14 by welding. This holder member 16 has a half-rounded groove lengthwise over the whole length.

The outer pipe 18 is a hollow pipe made from stainless steel and the like and has a small outer diameter of approximately 3 mm so as to pass easily through a cervical canal and has a length of approximately 50 cm while a part of which is omitted in FIGS. 1 and 2.

The semen injecting pipe 24 is a flexible translucent hollow tube of TEFLON® and the like and is selected from such flexible materials that can advance smoothly in the forward direction from the front end of the outer pipe 18 when the tube 24 is pinched with fingers and pushed forward at the rear of the outer tube 18.

Figure 3:
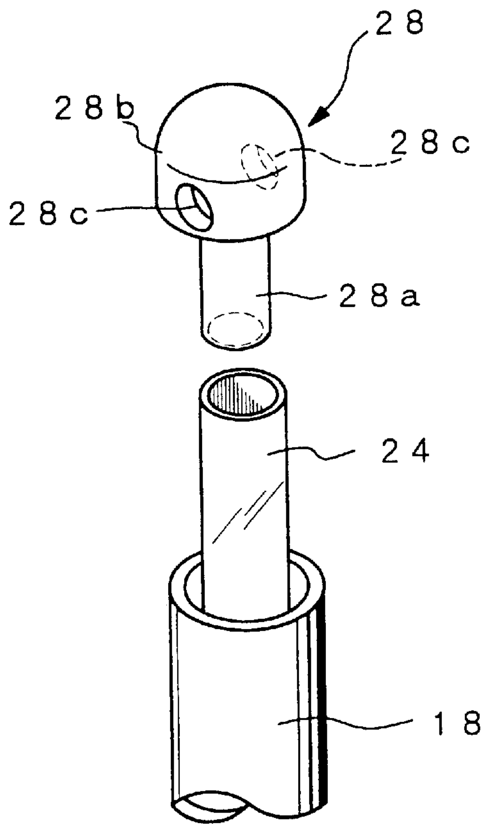
FIG. 3 is an enlarged view of a discharge nozzle in part A of FIG. 1.

At the tip of the semen injecting pipe 24 is mounted the injecting nozzle 28 as enlarged in FIG. 3. The injecting nozzle 28 is made from stainless steel and comprises a hollow tube part 28*a* fitted into the inner periphery of the front end of the tube 24 and a nozzle head 28*b* located at the front end of the tube part 28*a*. A base part at the lower end of the nozzle head 28*b* has the same outer diameter as that of the outer pipe 18. The nozzle head 28*b* has a hemispherically rounded front end and a pair of discharge openings 28*c* formed in the outer periphery of the nozzle head 28*b* oppositely at 180 degrees.

The semen injecting tube 24 is introduced from the aforementioned discharge nozzle 28 into the inside of the outer pipe 18 and goes out of the rear end of the outer pipe 18 to make approximately one turn there, and then is inserted from the small hole 12*b* of the front end of the heat-retaining tube 12 into the inside thereof, as shown in FIG. 2.

The syringe 22 has a function as a piston for pushing out semen in the straw 26. It is preferable that the syringe 22 contains drug liquid such as dextrose liquid and the like containing an effective substance for maintaining activity of sperm, whereby drug liquid is pushed out from the aforementioned discharge nozzle together with the semen.

The straw 26 is a polyethylene-made tube, one end of which is sealed and the other end of which is blocked by a cotton plug and in which semen of an ox is conserved by freezing. Both ends are cut off after thawing the semen, which are then connected to the syringe 22 and the tube 24 through the sockets 30 and 32, respectively.

Figure 4:
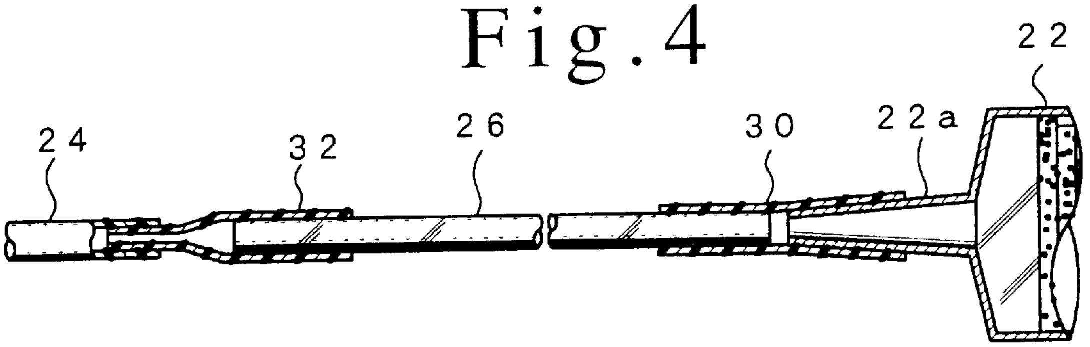
FIG. 4 is a partly enlarged view showing a state of connection of a straw in part B of FIG. 1.

FIG. 4 shows the state of connection of the straw 26. In FIG. 4, each socket 30, 32 is formed of high density polyethylene. One end of the socket 30 is in tapered-shape so as to adapt to taper of the nozzle of the syringe 22*a* and the other end is in somewhat small tapered-shape which is enlarged outward corresponding to the outer diameter of the straw 26.

One end of the other socket 32 is fitted to the outer periphery of the straw 26 and is actually in tapered-shape which is rather enlarged outward like the above although shown in the straight-shaped in FIG. 4. And the diameter of the other end is previously set so as to fit fixedly to the inner diameter of the tube 24.

There are two kinds of diameter of the straw 26, one is for 0.25 ml volume and the other is for 0.5 ml volume, both of which can be connected when the sockets 30 and 32 of different diameter are used.

In order to securely connect the outer pipe 18 to the heat-retaining tube 12, the protecting cover 14 is fitted to lower surface of the heat-retaining tube 12 and the rear end portion of the outer pip 18 is fitted to the holder member 16 of the protecting cover 14. Then, while maintaining the above fitting state by one hand, the pinch cock 20 is inserted with other hand from the front end of the outer pipe 18 and then the pinch cock 20 is moved to the outer surface of the aforementioned fitted three members while opening the pinchcock by pinching finger grips strongly. Thereafter, when the pinching force applied to the finger grips of the pinchcock is released, the outer pipe 18 is fixed to the heat-retaining tube 12 through the protecting cover 14 as shown in FIG. 2.

Each outer peripheral surface of the heat-retaining tube 12 and the outer pipe 18 is covered with a transparent plastic cover (bag) made of vinyl and the like in an assembled state so as to prevent contamination at initial stage of operation.

Next, operations for artificial insemination of semen using the aforementioned injector 10 will be described. First, before operations, the outer pipe 18 is mounted to the heat-retaining tube 12 by using the pinchcock 20 in such a manner as described above. At this time, the semen injecting tube 24 is made to occupy a retracted position so that the discharge nozzle 28 at the front end of the tube 24 can block the opening at the front end of the outer pipe 18. Next, a setting operation for the injector 10 is carried out according to the procedures as described below.

(1) The outer peripheral surface of the outer pipe 18 is covered with a vinyl cover 34 which is sealed at the front end thereof.

(2) The frozen semen is thawed. This operation is carried out in such a way that the straw is dipped in hot water the temperature of which is maintained at 37° C. for 12 seconds taking care not to increase semen temperature to 4° C. and above.

(3) The straw taken out is cleaned up with alcohol cotton. A sealed portion of the straw is held with fingers and is shaken lightly to collect layers of air in the sealed portion and the front end of the sealed portion is cut off by a straw cutter.

(4) A cutting section of the straw is fitted through the socket 30 to the nozzle 22*a* of the syringe 22 which has sucked 2 ml of dextrose liquid (drug liquid containing an effective substance for maintaining activity of sperm) in, the temperature of which has been previously maintained at room temperature.

(5) The cotton plug portion side is cut off by a straw cutter and connected to the tube 24 through the socket 32.

(6) The syringe 22 and the straw are inserted into the heat-retaining tube 12 from the rear end thereof. Thereby, the semen is not exposed to the air and the temperature of the semen can be maintained and deterioration of activity because of shock by temperature can be prevented.

(7) The outer periphery of the heat-retaining tube 12 is covered with a vinyl cover 36 which is sealed at the rear end thereof. At this time, the cover 34 of the outer tube 18 is inserted inside of the cover 36 of the heat-retaining tube 12 and overlapped portion of both is fastened by a binding line. The surplus portion 24*a* of the tube 24, which is a projecting part from the heat-retaining tube 12 and is rolled into nearly a circular shape, is housed in the vinyl cover 36 covering the heat-retaining tube 12.

Figure 5:
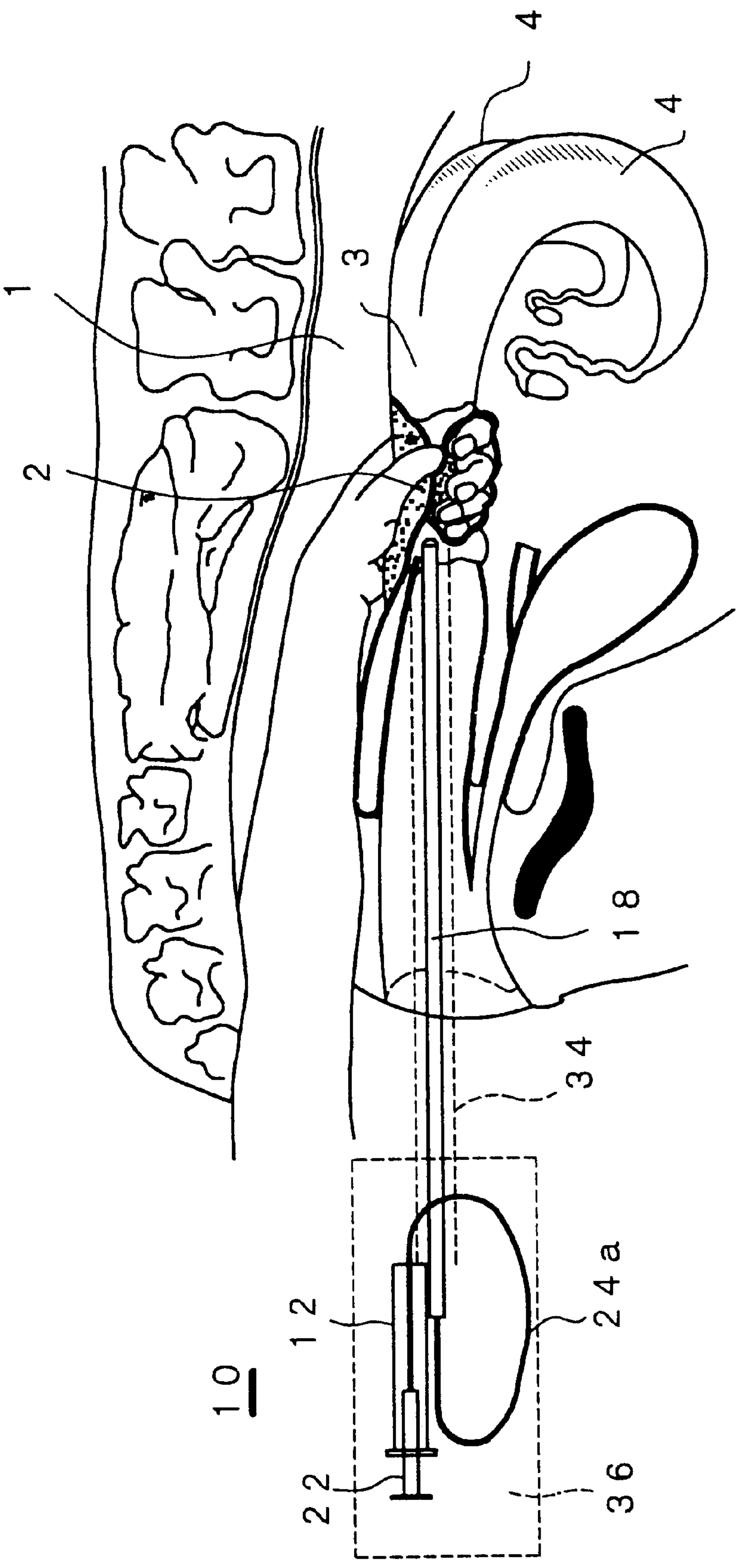
FIG. 5 is an explanatory pictorial view showing an initial stage of injection operation using an injector of the present invention.
Figure 6:
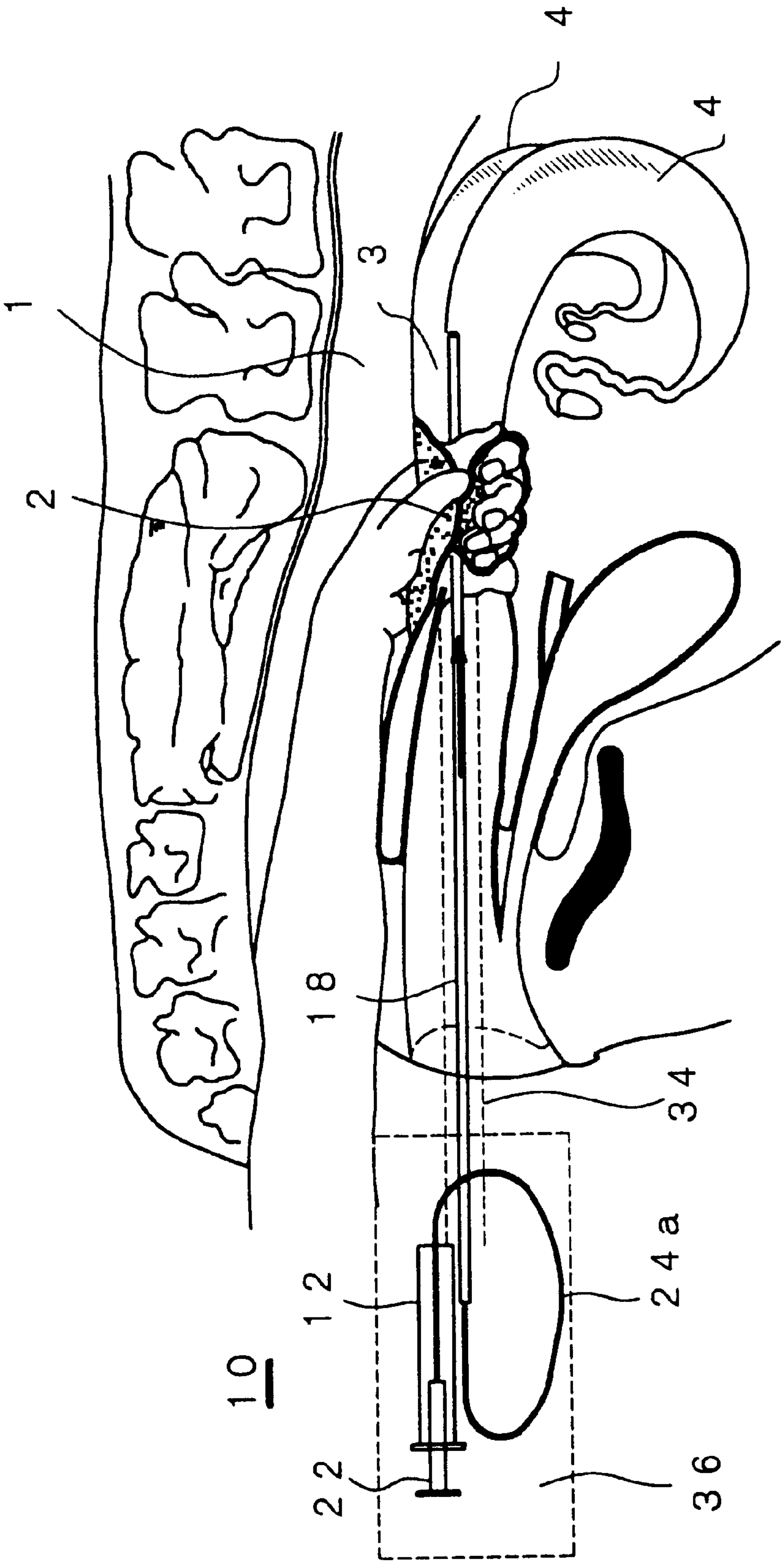
FIG. 6 is an explanatory pictorial view showing a mid-stream stage of injection operation using an injector of the present invention.
Figure 7:
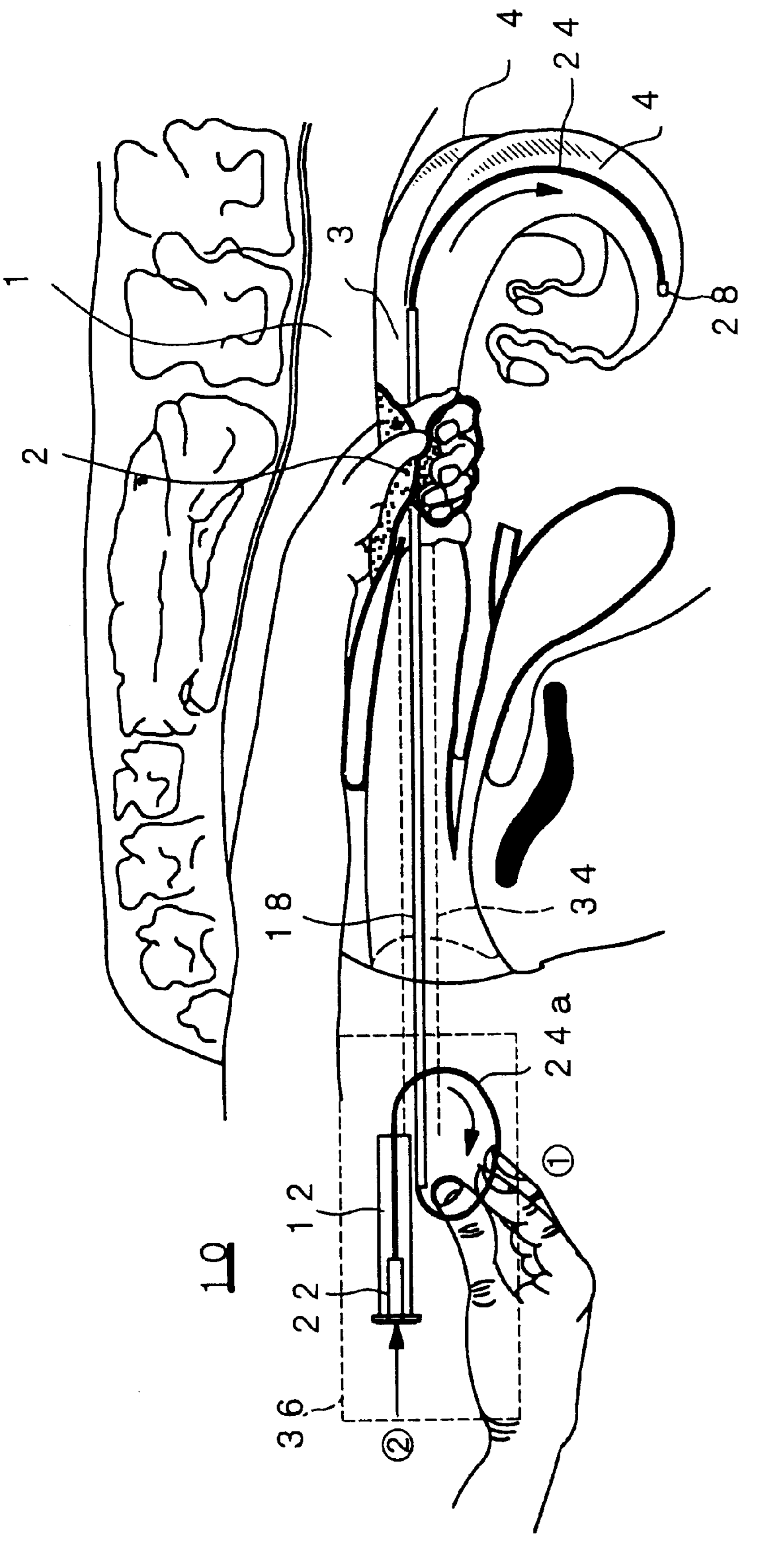
FIG. 7 is an explanatory pictorial view showing a final stage of injection operation using an injector of the present invention.

FIGS. 5 to 7 are explanatory pictorial views of fertilization operation by a rectovaginal method using the injector 10 just after assembling in such a manner as described above. In FIG. 5, the aforementioned vinyl covers 34 and 36 covering the outer peripheries of the outer pipe 18 and the heat-retaining tube 12 are shown in broken lines.

In this operation, as shown in FIG. 5, one hand is first inserted into a rectum 1 through an anus to grasp the cervical canal 2 through the rectum 1, then the outer pipe 18 of the semen injector 10 is inserted into the uterus by the other hand to pass through the cervical canal 2 while ascertaining a position of outer pipe 18 by feeling of hand at a position of the cervical canal 2.

When the outer pipe 18 has passed through the cervical canal 2, the outer pipe 18 is inserted further in about 5 cm toward the cornu uteri 4 at the side of ovulation as shown in FIG. 6. The side of ovulation in one of two cornu uteri 4 can be ascertained by touch on ovarium by a hand.

Figure 8A:
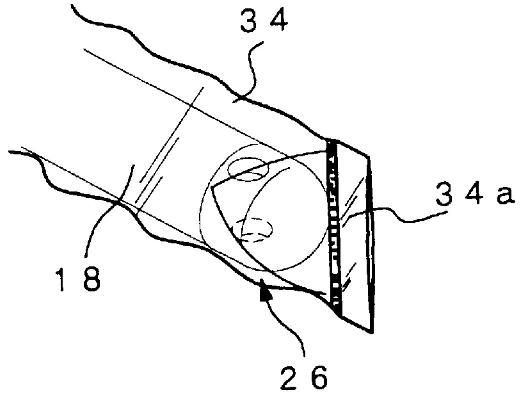
FIG. 8(*a*) is an explanatory pictorial view showing a state that a discharge nozzle is contained in a front end of a vinyl cover and FIG. 8(*b*) is an explanatory pictorial view showing a state that the discharge nozzle breaks and projects through the front end of the vinyl cover.
Figure 8B:
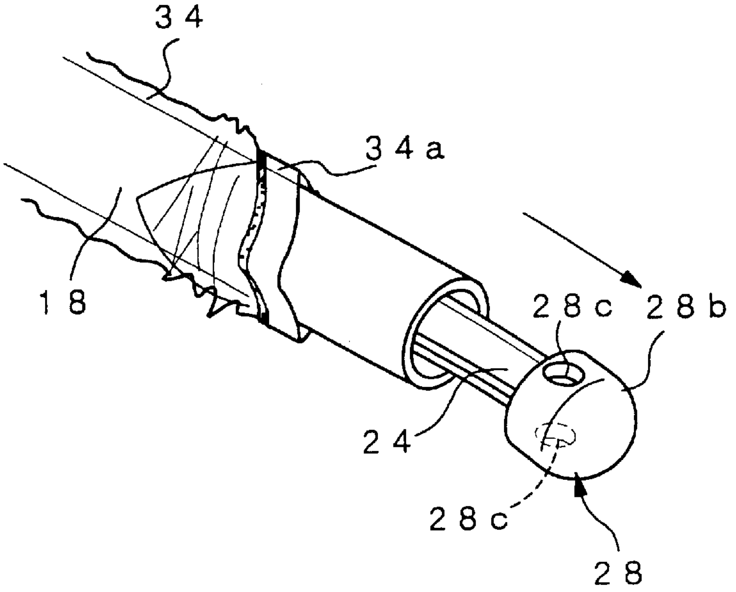

Next, as shown in FIG. 8 (*a*) and (*b*), the vinyl cover 34 covering the outer pipe is pulled back to make the top of the discharge nozzle 28 break the sealed front end 34*a* of the vinyl cover 34 and expose through the vinyl cover 34.

Next, as shown by reference numeral $\hat{1}$ in FIG. 7, the surplus portion 24*a* of the tube 24 rolled in a shape of loop is paid out carefully in the forward direction through the vinyl cover 36 by a hand for operating the injector 10 to push out the discharge nozzle 28 from the front end of the outer pipe 18.

When the discharge nozzle 28 is pushed out in such a manner as described above, the nozzle head 28*b* reaches to the depths of the cornu uteri 4 while touching soft the endometrium as shown in FIG. 7, because the specific gravity of the nozzle head 28 is considerably higher than that of the tube 24 as the nozzle head 28 is made from stainless steel, thereby curving the tube downward. While a rough measure of the length of the tube 24 paid out is 15 to 20 cm for a parous cow and 10 to 15 cm for an unparous cow, it is adjusted depending on an individual difference. This length of the tube 24 paid out can be easily known by a mark printed on the tube.

When the tube 24 is paid out in a given length in such a manner as described above, a piston of the syringe 22 is pushed as shown by reference numeral $\hat{2}$ in FIG. 7. Thereby, the semen is discharged from the discharge opening 28*c* of the nozzle head 28*b* through the tube 24 and injected to the depths of the uterus 4. In this case, the semen is first injected and then the effective substance for maintaining the activity of the sperm such as dextrose liquid and the like is injected while washing out the remaining sperm, of which situation can be visually observed through the vinyl cover 36 and the heat-retaining tube 12.

According to an actual result, it is ascertained that good embryogeny can be obtained even if the number of sperm is one 200 th of that of convention. Finally, the tube 24 is pulled back to sheathe it in the outer pipe 18 which is then pulled out from the uteri 3 and the operation is completed.

Thereafter, the syringe 10 is disassembled as shown in FIG. 1 and is washed, sterilized and disinfected, thereby enabling reuse.

While a case where the injector of the present invention is applied to artificial insemination for a cow is described in the aforementioned preferred embodiments, the preferred embodiments are available for transplantation of an ovum of a cow in the same manner. And they are available not only for a cow, but also for an animal such as a horse and any others to which a rectovaginal method can be applied.

Figure 9:
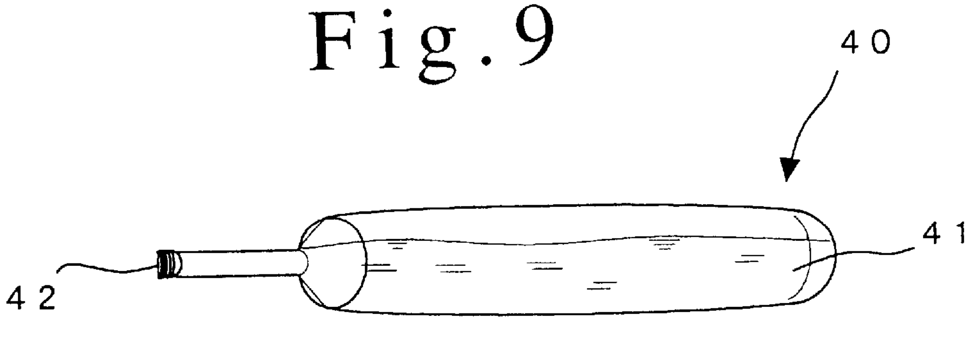
FIG. 9 is a perspective view showing an example of variation of a syringe used for an injector of the present invention.
Figure 10:
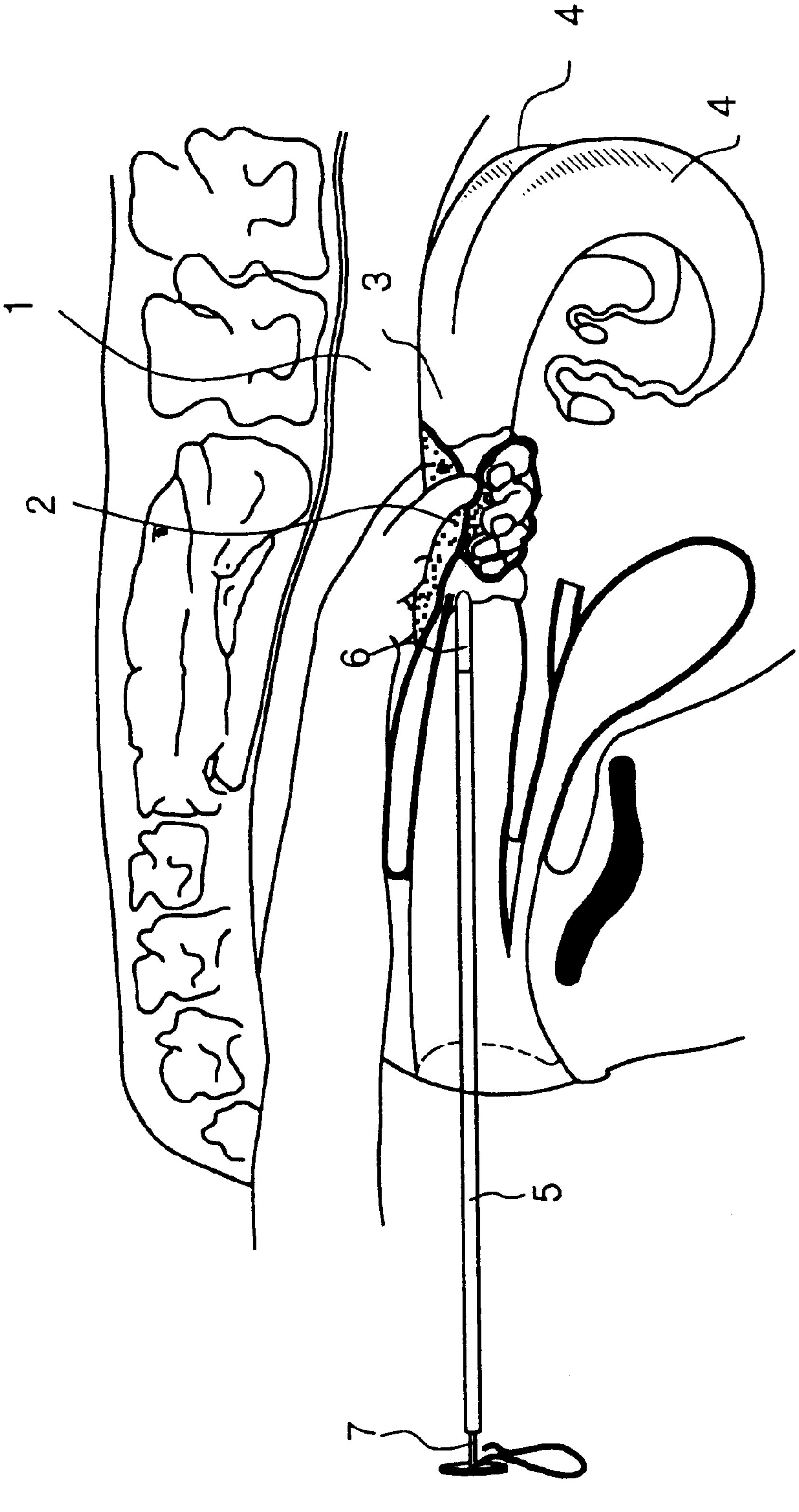
Fig. 10 PRIOR ART
FIG. 10 is an explanatory pictorial view showing a semen injecting operation by a rectovaginal method using a conventional semen injector.

The injector of the present invention is not limited to the aforementioned preferred embodiments, but may be made in various kinds of modifications, for example, the syringe may be constructed of a capsule-shaped transparent or translucent plastic container 40 comprising a body and a neck as shown in FIG. 9. It is possible that the drug liquid 41 containing effective substances such as dextrose liquid for activation of a sperm or of an ovum is previously injected in the body of the plastic container 40 and the front end 42 of the neck is crushed flat to form the airtight seal, and the front end of the neck is cut off when using to which the straw is mounted through the socket 30 as shown in the aforementioned preferred embodiments. While this plastic container 40 is preferably selected from plastic deformable materials such as celluloid and the like, it is necessary that a member is mounted for maintaining deforming state so as not to return to original state after elastic deformation when using an elastic deformable plastic.

Apparently from the aforementioned descriptions, the following effects can be obtained.

Since the flexible tube is inserted directly through inside of the outer pipe, the outer diameter of the outer tube can be diminished so that it can be easily inserted without injuring cervical canal. Also, since the flexible tube paid out forward from the outer pipe bends downward owing to the weight of the nozzle body of its front end, it goes surely into a cornu uteri and thereafter is inserted into the depths of the cornu uteri along a curve of the cornu uteri. Comparing the injector of the present invention with a conventional sperm injector, it was ascertained that good result of present insemination can be obtained even if the number of sperm is one 200 th of that of convention.

In a preferred embodiment of the invention, since the contact of the sperm or ovum with the air is interrupted in the heat-retaining tube when operation is carried out in the air of relatively low temperature, the inactivation of the sperm or ovum by temperature shock can be prevented. Since the heat-retaining tube is made from transparent materials, the situation that the sperm or ovum is pushed through inside of the transparent or translucent tube by means of a pushing means can be visually observed. Also, since the tube goes out of the rear end of the outer pipe and makes approximately one turn, the operation of paying out the tube into the outer pipe by pinching this portion with fingertips can be easily carried out. If the length of surplus portion of this tube making one turn is matched with the length of the tube paid out from the front end of the outer tube, the length of the tube which is to be paid out can be easily grasped. Furthermore, if a scale is marked to the surplus portion of the tube, the length of the tube paid out can be more easily ascertained.

In a preferred embodiment of the invention, since a thawed straw can be mounted to the tube, the conventional operation for taking out once an ovum from the straw and sucking it into the tube is omitted, and as a result, improvements in operability and survival rate of an ovum can be extremely made.

In a preferred embodiment of the invention, the situation in which the sperm or ovum is pushed in the tube can be visually observed by making the tube from transparent or translucent material.

In a preferred embodiment of the invention, the injector of the present invention can be fitted to the straw of a various kinds of diameter without changing another parts.

In a preferred embodiment of the invention, since the effective substances for maintaining the activity of the sperm or ovum is injected from the tip of the nozzle body in a state of mixture with the sperm or ovum, the insemination rate or embryogeny rate and be improved.

Although the preferred embodiments of the present invention have been described, many modifications and alterations may be made within the spirit of the present invention.

What is claimed is:

1. An injector of a sperm for artificial insemination or a fertilized ovum for transplantation of a domestic animal comprising an outer pipe, a flexible tube inserted and placed inside of said outer pipe to be freely pushed out, a nozzle body mounted integrally to a front end of said flexible tube, said nozzle body having a closed front end which is formed in a shape of spherical surface and having a rear end connected to said flexible tube, said nozzle body further having in a side of said nozzle a perforated hole connected to said flexible tube, and a pushing means adapted to be connected with a rear end of said flexible tube for sending forward the sperm or ovum, said flexible tube being pushed forward from the rear end of said outer pipe after insertion of said outer pipe into a corpus uteri of the domestic animal, thereby paying out said flexible tube forward from the front end of said outer pipe to send said nozzle body to a deep portion of a cornu uteri and thereafter to discharge the sperm or ovum from said perforated hole of said nozzle body into the deep portion of said cornu uteri through inside of said flexible tube by said pushing means.

2. An injector of a sperm for artificial insemination or a fertilized ovum for transplantation of a domestic animal as claimed in claim 1, wherein said flexible tube extends outside beyond the rear end of said outer pipe, the extended part of said flexible tube allowing to be pinched by: finger tips and pushed forward by said finger tips.

3. An injector of a sperm for artificial insemination or a fertilized ovum for transplantation of a domestic animal as claimed in claim 2, wherein a heat-retaining tube is fitted to an outer peripheral surface of the rear end of said outer pipe, and the rear end of said flexible tube extends rearward from the rear end of said outer pipe and goes into said heat-retaining tube from the front end of said heat-retaining tube by making approximately one turn between said outer pipe and said heat-retaining tube.

4. An injector of a sperm for artificial insemination or a fertilized ovum for transplantation of a domestic animal as claimed in claim 3, wherein said one turn of said flexible tube defines a length of the flexible tube to be paid out from the front end of said outer pipe, said length of said flexible tube corresponding to the distance from the inside of the cervical canal to the deep portion of the cornu uteri.

5. An injector of a sperm for artificial insemination or a fertilized ovum for transplantation of a domestic animal as claimed in claim 3, comprising a straw containing a sperm or ovum and removably attached between the rear end of said flexible tube and said pushing means to be contained in said heat-retaining tube.

6. An injector of a sperm for artificial insemination or a fertilized ovum for transplantation of a domestic animal as claimed in claim 3, wherein said heat-retaining tube is made from a transparent material.

7. An injector of a sperm for artificial insemination or a fertilized ovum for transplantation of a domestic animal as claimed in claim 5, wherein socket members adaptable to straws of different calibers is mounted removably to the front end and rear end of said straw respectively, and said straw is joined to said flexible tube and said pushing means respectively through said each socket member.

8. An injector of a sperm for artificial insemination or a fertilized ovum for transplantation of a domestic animal as claimed in claim 1, wherein an effective substance for maintaining activity of a sperm or an ovum is previously injected into said pushing means before said straw is joined.

9. A method of operating an injector of a structure as claimed in claim 3, wherein an outer periphery of said outer pipe is covered with a first plastic bag which is watertight, transparent and thin and the front end of which is sealed, an outer periphery of said heat-retaining tube is covered with a second plastic bag which is watertight, transparent and thin and the rear end of which is sealed, and said outer pipe of said injector is inserted in a given length into a uterus of a domestic animal in a state that an overlapped portion of both transparent plastic bags is sealed through a banding means, then said first plastic bag is moved relatively to said outer pipe to break a sealed portion of the front end of said first plastic bag, thereafter said flexible tube is picked with fingertips from outside of said second plastic bag, thereby pushing to send forward said flexible tube.

* * * * *